United States Patent [19]
Guglielmi

[11] Patent Number: 5,916,235
[45] Date of Patent: Jun. 29, 1999

[54] APPARATUS AND METHOD FOR THE USE OF DETACHABLE COILS IN VASCULAR ANEURYSMS AND BODY CAVITIES

[75] Inventor: Guido Guglielmi, Santa Monica, Calif.

[73] Assignee: The Regents of the University of California, Oakland, Calif.

[21] Appl. No.: 08/910,645

[22] Filed: Aug. 13, 1997

[51] Int. Cl.$^6$ .................................................... A61M 29/00
[52] U.S. Cl. ............................ 606/200; 606/33; 606/194
[58] Field of Search ................................. 606/127, 128, 606/200, 198, 113, 191, 47, 33, 41, 194; 623/1

[56] References Cited

U.S. PATENT DOCUMENTS

| | | | |
|---|---|---|---|
| 5,397,320 | 3/1995 | Essig et al. | 606/127 |
| 5,496,330 | 3/1996 | Bates et al. | 606/127 |
| 5,522,836 | 6/1996 | Palermo | 623/1 |
| 5,611,803 | 3/1997 | Heaven et al. | 606/47 |

*Primary Examiner*—Michael Buiz
*Assistant Examiner*—Julian W. Woo
*Attorney, Agent, or Firm*—Daniel L. Dawes

[57] ABSTRACT

The retention of free coils or GDC coils within body cavities or aneurysms in the human vascular system is achieved through the use of a GDC cage. The GDC cage is comprised of an expandable cage coupled to the wire, which cage and wire are disposed within a catheter. The cage has a memory so that it normally assumes an expanded configuration when unconfined, but is capable of assuming a collapsed configuration when disposed and confined within the catheter. In the illustrated embodiments a detachable joint is provided between the cage and wire so that the cage may be selectively detached from the wire and left in place within the body lumen in its selected position in the expanded configuration. The cage may thus be placed and detached in aneurysms to retain the coils disposed therein or placed in front of aneurysm openings to prevent the escape of free coils from the aneurysm. The cage may be used as a fishing tool to capture escaped free coils in the vessel, which may have escaped from the aneurysm. In addition, RF energy may be applied to the cage so that when the cage is placed in a large body lumen, it serves as a collapsible RF antenna. As the body lumen shrinks on the cage, the cage compliantly yields while continuing to deliver RF energy to the body lumen until the desired amount of shrinkage is obtained.

19 Claims, 4 Drawing Sheets

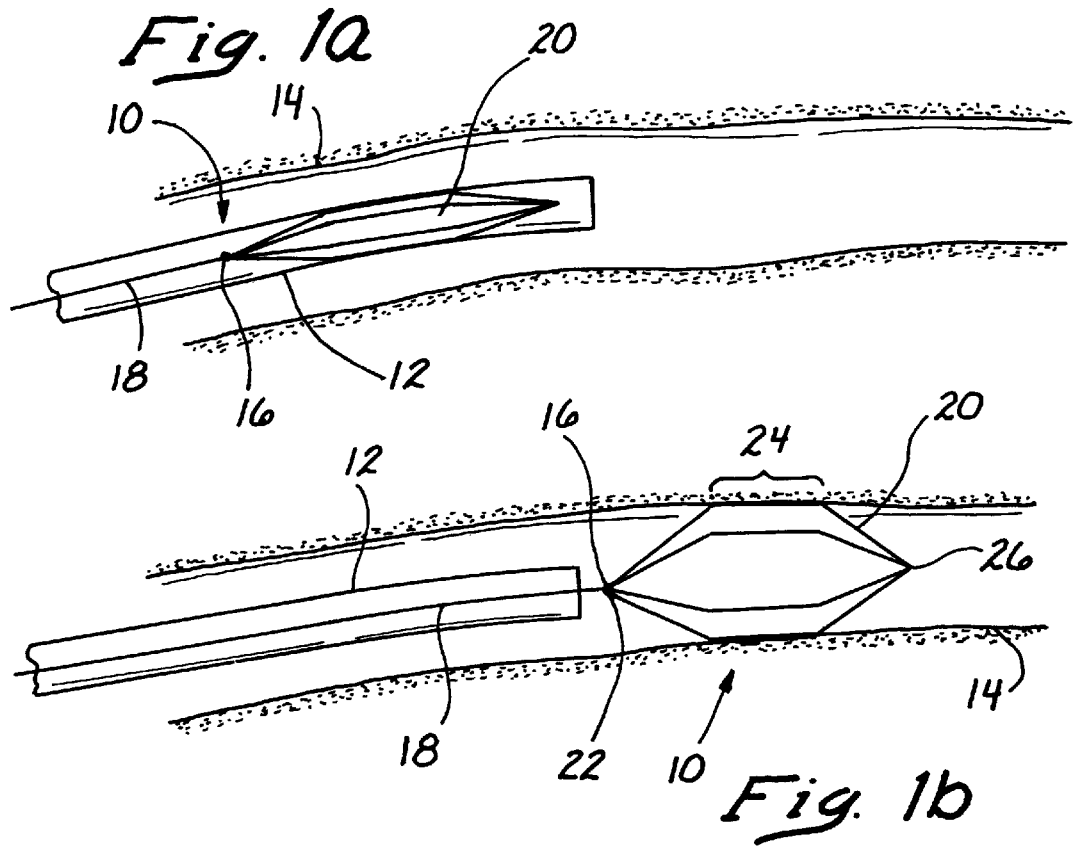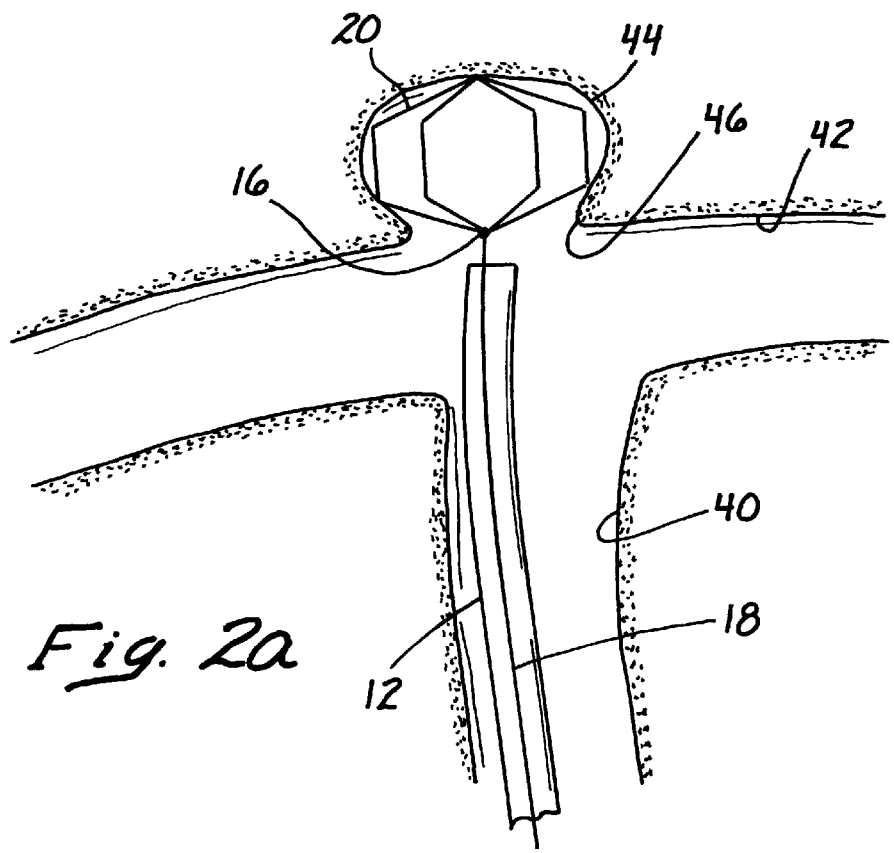

APPARATUS AND METHOD FOR THE USE OF DETACHABLE COILS IN VASCULAR ANEURYSMS AND BODY CAVITIES

BACKGROUND OF THE INVENTION

1. Field of the Invention

The invention relates to devices used for treatment within various body cavities and, in particular, to treatment of intracranial aneurysms.

2. Description of the Prior Art

Approximately 25,000 intracranial aneurysms rupture every year in North America. The general method of treatments intracranial aneurysms are extravascular, intravascular and extra-endovascular. The extravascular treatment is comprised of invasive surgery or microsurgery of the aneurysm to preserve the artery. The extra-endovascular comprises invasive surgery to expose the aneurysm to perforate it from the outside and to use various techniques to occlude the interior to prevent rebleeding.

An intravascular treatment has recently been developed, using navigable microcatheters to implant a plurality of small coils and/or to apply an electrical current through a coil which occludes or partially occludes the aneurysm and which is then detached with the result that the aneurysm is entirely occluded and rebleeding prevented. Such detachable coils are known as GDC coils or Guglielmi Detachable Coils based upon technology described in U.S. Pat. Nos. 5,122,136 (1992); 5,354,295 (1994); 5,540,680 (1996) and others, which are incorporated herein by reference. Therefore for the purposes of this specification and claims a "GDC coil" shall be defined to mean any device having a detachable coil for endovascular placement and in particular shall include the devices disclosed in the foregoing patents While the intravascular treatment of aneurysms or occlusion of a bodily cavities has been successfully treated with GDC coils, in some patient cases the multiple insertion of GDC coils in the aneurysm or cavity has been difficult, because of the size of the aneurysm or of the neck or entrance to the aneurysm and because of the number of coils which needed to be inserted and retained in the aneurysm. In the case of a large number of coils, or in the case of a large opening to the aneurysm, the possibility of one or more coils escaping into the vascular system increases. Disposition of the coil at an uncontrolled site can give rise to a potential uncontrolled and, perhaps, undesired occlusion.

Therefore, what is needed is some type of apparatus and method whereby multiple GDC coils may be employed in the vascular system or in other bodily cavities and either retained within the aneurysm or cavity or at least easily retrieved in the event that it should escape.

BRIEF SUMMARY OF THE INVENTION

The invention is defined as an apparatus for use within a body lumen comprising a wire, a selectively detachable joint, and an expandable cage. The joint selectively couples the cage to the wire. The expandable cage is capable of assuming a collapsed and expanded configuration. The expanded configuration is self-assumed by the cage when the cage is freed of confinement. As a result, the cage expands for deployment within the body lumen.

The apparatus further comprises a catheter. The wire and expandable cage are selectively disposable within the catheter when the cage assumes the collapsed configuration. When the cage is selectively disposed outside of the catheter, the cage assumes the expanded configuration.

In one embodiment the body lumen includes a cage and at least one coil disposed in the cage such that the cage retains the coil in the body lumen. For example, the body lumen is an aneurysm and the coil is disposed in the aneurysm. The catheter is used to position the cage into the aneurysm. The cage assumes the expanded configuration as the cage is disposed from the catheter into the aneurysm. The coil is then disposed into the aneurysm and retained in the aneurysm by the cage.

In another embodiment the cage is disposed from the catheter across the opening of the aneurysm in the parent vessel. The cage acts as a retaining grate across the opening to prevent escape of coils from the aneurysm.

In another application the body lumen is a vessel and the free coil is disposed in the vessel. The cage captures the free coil in the vessel when the cage is in the expanded configuration and allows the captured free coil to be removed with the cage from the vessel by pulling the cage into the catheter capturing the free coil.

In still another application the apparatus further comprises a source of radio frequency energy coupled to the wire so that the radio frequency energy is coupled to and emitted from the cage into the body lumen to diathermally heat and thereby shrink the body lumen, while the cage tends to assume the collapsed configuration according to shrinkage of the body lumen.

The cage is comprised of a plurality of wires having a memory so that when the cage is free of confinement, it assumes a prebiased shape memorized by the plurality of wires. In one embodiment the cage is comprised of a plurality of wires in the form of a cylindrical barrel. The cylindrical barrel cage has a bottom and top apex where the plurality of wires are commonly joined together.

In other embodiments the cage comprises a helical coil or at least one randomly-shaped coil or wire, which when in its free or expanded configuration, is contained within an envelope of a predetermined shape such as double, back-to-back cones or a spherical envelope.

In another embodiment the cage comprises a plurality of wire. One end of each of the wires is coupled together in a common apex and opposing ends of which are free. The opposing free end forms a curved hook shape.

In some of the embodiments the detachable joint is electrolytically disintegrated to detach the wire from the cage. The detachable joint is thus an electrolytically disintegratable region or may be provided as an electrolytically disintegratable bead. The electrolytically disintegratable region comprises a flexible electrolytically disintegratable coil coupled between the wire and the cage. The electrolytically disintegratable region further comprises a tapered tip of the wire extending through the coil and coupled to the cage.

The invention is also an RF probe for shrinking a body lumen comprising a wire, an expandable cage coupled to the wire, the cage capable of assuming an expanded configuration and a collapsed configuration, including a continuous deformation of configurations therebetween. The cage is adapted to deliver radio frequency energy to tissues surrounding the body lumen to diathermally heat and shrink the tissue and lumen. The cage has a resiliency so that when it is free of confinement, the cage normally assumes the expanded configuration and then assumes the collapsed configuration without providing any material impediment to the shrinkage of the body lumen when confined by the shrinking lumen.

The invention is still further a fishing tool for retrieval of foreign introduced bodies in a body lumen comprising a wire and an expandable cage coupled to the wire. The cage is biased to assume an expanded configuration when unconfined and is capable of assuming a collapsed configuration when confined. The expanded cage provides a plurality of surfaces for coupling with or capturing the foreign body without substantially impeding fluid flow through the body lumen.

The fishing tool further comprises a catheter. The cage and wire are deliverable to the body lumen through the catheter. The cage is confined and collapsed when disposed in the catheter and is unconfined and expanded when disposed out of the catheter. The foreign body is a free coil and the cage comprises a plurality of wires in a three dimensional array adapted to snare the free coil.

The invention now having been briefly summarized, it is illustrated in its various embodiments as set forth in the following drawings where like elements are referenced by like numerals.

BRIEF DESCRIPTION OF THE DRAWINGS

FIG. 1a is a diagrammatic cut-away side elevational view of a first embodiment of the invention in which the GDC cage of the invention is disposed within a micro-catheter within a vessel in an undeployed configuration.

FIG. 1b is a diagrammatic cut-away side elevational view of the embodiment of FIG. 1a in which the GDC cage has been deployed into the vessel.

FIGS. 2a–d are diagrammatic cut-away side elevational views of the deployment of the first embodiment of the GDC cage inside of an endovascular aneurysms and subsequent deployment of the GDC coils with the cage.

Figure 2B:
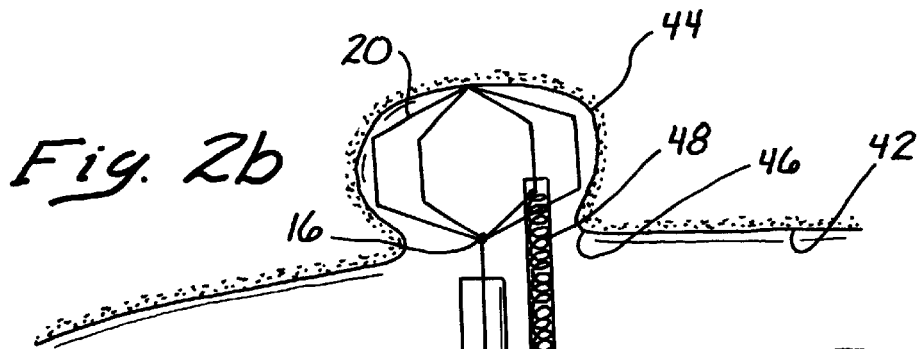

The invention, having been illustrated by way of example in the foregoing drawings, can now better be understood by turning to the following detailed description:

DETAILED DESCRIPTION OF THE PREFERRED EMBODIMENTS

The retention of free coils or GDC coils within body cavities or aneurysms in the human vascular system is achieved through the use of a GDC cage. The GDC cage is comprised of an expandable cage coupled to the wire, which cage and wire are disposed within a catheter. The cage has a memory so that it normally assumes an expanded configuration when unconfined, but is capable of assuming a collapsed configuration when disposed and confined within the catheter. In the illustrated embodiments a detachable joint is provided between the cage and wire so that the cage may be selectively detached from the wire and left in place within the body lumen in its selected position in the expanded configuration. The cage may thus be placed and detached in aneurysms to retain the coils disposed therein or placed in front of aneurysm openings to prevent the escape of free coils from the aneurysm.

The cage may also be used as a fishing tool to capture escaped free coils in the vessel, which may have escaped from the aneurysm.

In addition, RF energy may be applied to the cage so that when the cage is placed in a large body lumen, it serves as a collapsible RF antenna. As the body lumen shrinks on the cage, the cage compliantly yields while continuing to deliver RF energy to the body lumen until the desired amount of shrinkage is obtained.

FIGS. 1a and 1b diagrammatically illustrate a side cut-away view of the GDC cage assembly 10 disposed within a microcatheter 12 within a vessel or artery 14. GDC cage assembly 10 is comprised of a guidewire or delivery wire 18 and a cage 20. Although the following description will be described in connection with the vascular system and is to be expressly understood that the invention may be used in any type of body lumen or cavity and either in or outside of a blood or fluid environment. GDC cage 20 is coupled through a detachment joint 16 to a guidewire or delivery wire 18 which extends to the proximal end of micro-catheter 12 which is available for micromanipulation. Cage assembly 10 includes an expandable structure 20 coupled to wire 18 through detachment joint 16, which expandable structure 20 is shown in the illustrations of FIGS. 1a–6b as a barrel or bird cage with two conical ends and a circular cylindrical mid-portion. The structural details of cage 20 will be described in greater detail below in connection with FIGS. 6a and 6b. The envelope shape of cage 20 may further assume a variety of other shapes and structures as discussed in connection with FIGS. 7–9 or as may be derived in any manner now known or later devised consistent with the teachings of this invention. For the purposes of simplicity of illustration, GDC cage assembly 10 will be shown diagrammatically as having the bird cage structure in the illustrations of FIGS. 1a–5b although this is not be construed as necessarily limiting.

Cage 20 is comprised of a plurality of wires formed to have a memory defining the shape or envelope of cage 20. Typically cage 20 is comprised of a plurality of wires such as heat-treated platinum, Nitinol, a Nitinol alloy wire, stainless steel, plastic wires or other wire materials. In the case of plastic or substantially nonmetallic wires, it is assumed that the wire will be loaded with a radioopaque substance to allow its use with conventional fluoroscopy. In the illustrated embodiment of FIGS. 1a and 1b, cage 20 includes a plurality of wires joined at a proximal end 22 either to each other or to a solder joint and expanding or extending therefrom to form an equatorial section 24 and then converging again to be joined or to meet at an apex 26. The simple wires comprising structure 20 may be soldered, crimped or rolled together at end 22 and apex 26 or joined together in any other fashion desired. As shown in FIG. 1b, GDC cage 10 is advanced distally out of micro-catheter 12, thereby releasing cage 20 from the restriction of the confining walls of catheter 12 and to allow cage 20 to expand to its full memorized expanded shape, restricted, if at all, only by surrounding tissue or walls of vessel 14.

As will be described in connection with the application shown in FIGS. 2–5b below, GDC cage 20 is thereafter selectively detached from wire 18, which is then withdrawn together with catheter 12. The detachment of GDC cage 20 from wire 18 at joint 16 may be accomplished by electrolytic detachment, mechanical detachment, thermal detachment or any other means now known or later devised for endovascular detachment of a distal tip of a wire or probe. In the illustrated embodiment, the same electrolytic detachment techniques as used with GDC coils are also employed with GDC cage assembly 10.

Figure 4:
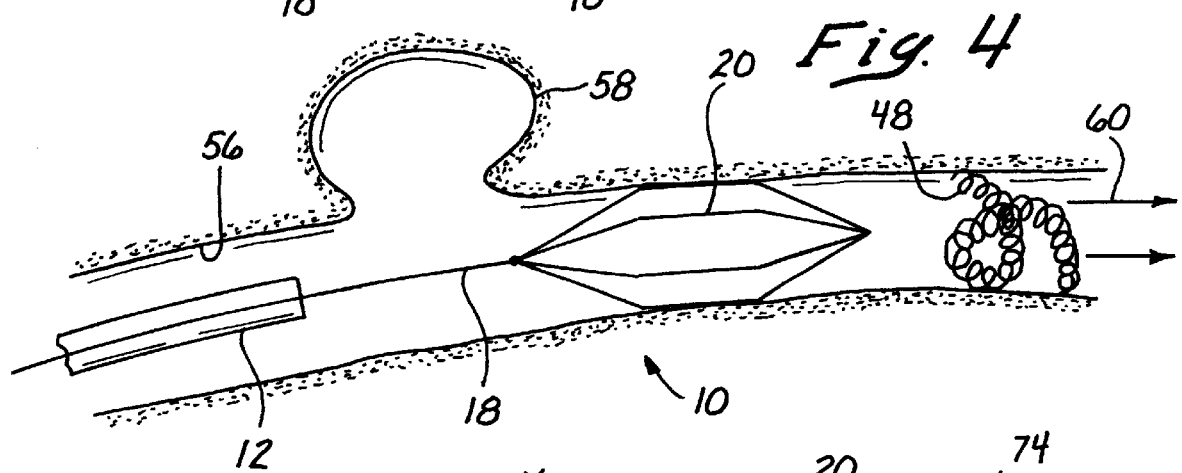
FIG. 4 is a diagrammatic cut-away side elevational view of the first embodiment of the GDC cage being used as a fishing tool or retrieving device to capture an escaped GDC coil.
Figure 5A:
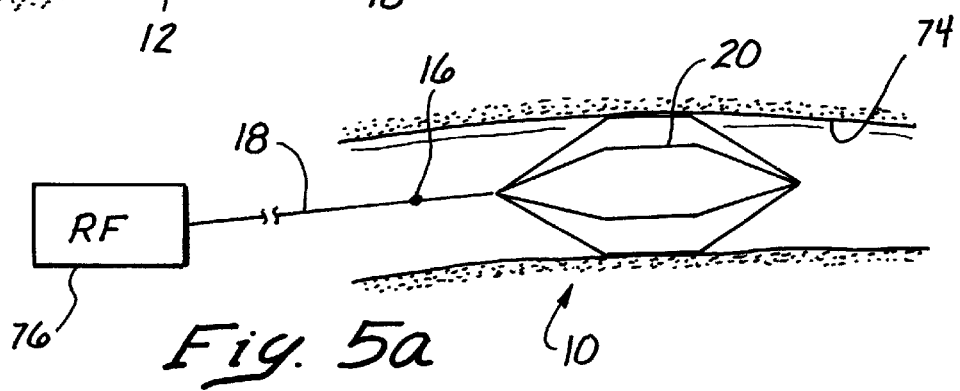
FIG. 5a is a diagrammatic cut-away side elevational view of the first embodiment of the GDC cage used as a radio-frequency probe to shrink the diameter of a large lumen shown in the pre-shrunk configuration.
Figure 5B:
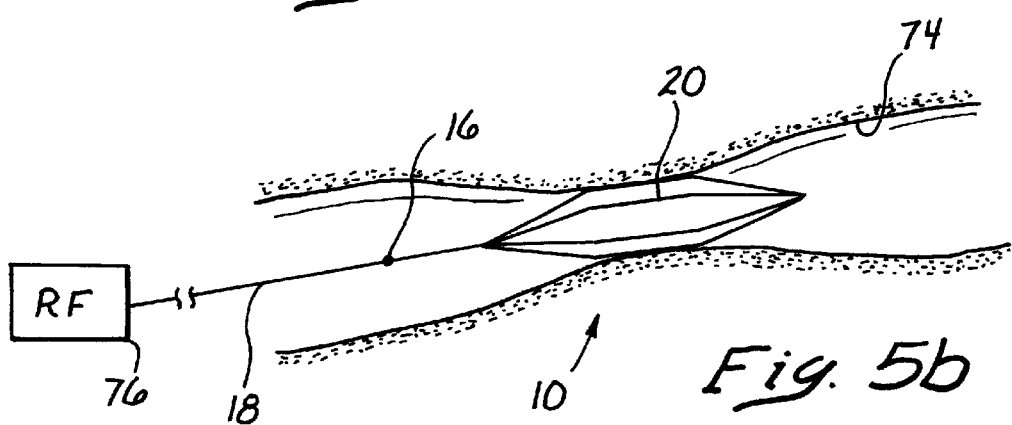
FIG. 5b is a diagrammatic cut-away side elevational view of the first embodiment of the GDC cage of FIG. 5a after the RF energy has been applied and the lumen has been shrunk.
Figure 6A:
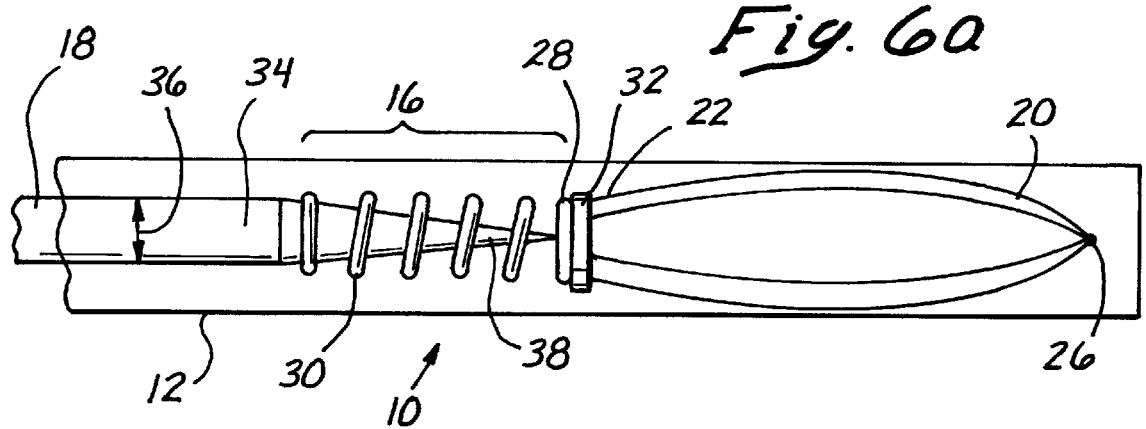
FIG. 6a is a cut-away side elevational view of the first embodiment of the GDC cage shown in enlarged scale and in greater detail as attached to a guide-wire and disposed in a micro-catheter in the undeployed configuration.
Figure 6B:
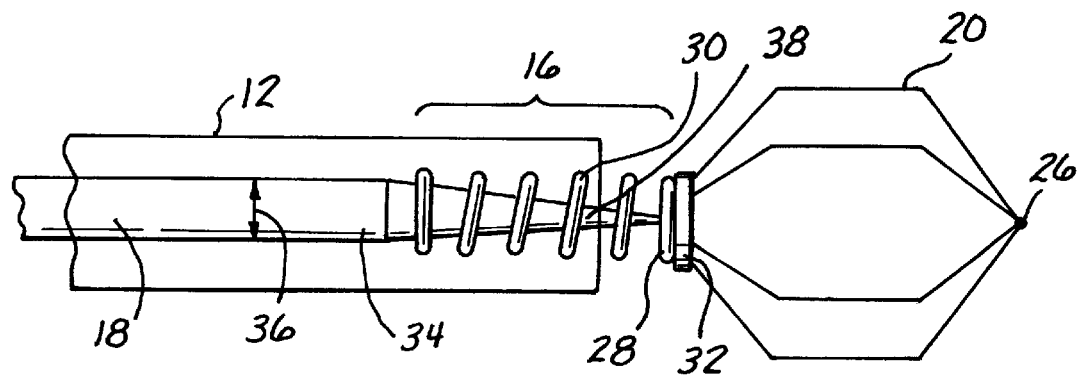
FIG. 6b is a cut-away side elevational view of the first embodiment of the GDC cage shown in enlarged scale and in greater detail attached to a guide wire deployed outside of the catheter.

Before considering the applications of GDC cage assembly 10 as shown in FIGS. 2–5b, turn and consider the greater structure detail of GDC cage assembly 10 as shown in FIGS. 6a and 6b. FIG. 6a shows GDC cage 10 connected to wire 18 in the undeployed configuration whereas FIG. 6b shows it deployed from the end of microcatheter 12. In the embodiment of FIGS. 6a and 6b, wire cage 20 is comprised of a plurality of wires joining or meeting at or near an apex 26 and attached at their opposing proximal ends 22 to the last circular or helical wrap 28 of a stainless steel helical coil 30. The wires of cage 20 are in the illustrated embodiment soldered to wrap 28, thereby forming a soldered joint 32. The opposing end of coil 30 is coupled or soldered to wire 18 at or about a position 34 where wire 18 assumes its normal or maximum diameter 36, which characterizes the predominant part of the length of wire 18 from the vicinity of its connection to coil 30 to its proximal end. Beginning at about position 34 on wire 18, wire 18 is characterized by a tapered reduction in its diameter from diameter 36 to a minimum diameter where wire 18 is coupled to soldered joint 32. This entire region can be characterized as the detachment region or joint 16. The degree of taper is variable according to design option and may be non-uniform so that wire 18 quickly reduces to a hair diameter, having tensile strength but little rigidity. Wire 18 is similarly comprised of stainless steel and together with flexible coil 30 presents a region of higher electrolytic susceptibility as compared to the less electrolyzable nature of platinum or Nitinol which forms the wires of cage 20 and solder joint 32. Therefore, some point within detachment region 16 will be the first to completely electrolyze and disconnect cage 20 from the remainder of wire 18. For example, in one embodiment, wire 18 has a diameter of approximately 0.25 mm, coil 30 is a helical coil with an inner diameter of approximately 0.25 mm formed from solid wire of approximately 0.05 mm in diameter and tapered region 38 has a length of approximately 1 cm and tapers down to a diameter of approximately 0.1 mm. The dimensions of any particular embodiment will vary according to the nature of the medical application in which cage assembly 10 is being used. The sizes of cage assembly 10 being generally much smaller in the case of endocranial applications as given above than in other applications, such as fallopian tubes.

As shown by the comparison of FIGS. 1a and 1b, wire cage 20 is expanded when extended out of the end of microcatheter 12, which also exposes at least the adjacent portion of detachment joint 16. The deployment illustrated in FIG. 1b will therefore tend to expose only the tip portion of detachment joint 16 and therefore concentrate or localize the electrolytic detachment at that joint. Alternatively, portions of detachment joint 16 and wire 18 may also be provided with a thin passivating layer which will electrically insulate the underlying material from the surrounding fluid or blood and thereby prevent or substantially retard any electrolytic action on the underlying material. For example, in this way wire 18 may be provided with an insulating film that passivates or protects it from any material electrolytic action and therefore concentrates and ensures that the electrolytic action and detachment occurs at defined joint 16 only.

GCD cage assembly 10 has been shown with a tapered region 38, extending from wire 18 to cage 20. However, it is expressly contemplated that tapered region 38 may be omitted and the sole connection between cage 20 and wire 18 may be by means of coil 30. The primary purpose for connection with tapered region 38 is to prevent elongation for deformation of GDC cage 20 when GDC cage assembly 10 is withdrawn from microcatheter 12 or otherwise manipulated in any manner which may tend to apply a tensile force stretching cage 20 away from wire 18. Since coil 30 is very flexible, pliable and soft with little resiliency in order to prevent any prebiased force or orientation being imparted by coil 30 to cage 20, it can also be easily deformed and stretched unless both stretching and compression are in some degree limited by tapered section 38 of wire 18. Although tapered section 38 has a relatively high tensile strength and a degree of resistance to compression, it is also a thin enough so as to not materially interfere with the lateral flexibility of the tip of GDC cage assembly 10. Any type of flexible coupling between wire 18 and cage 20 may be employed, including a tapered section 38 omitting coil 30.

Figure 2C:
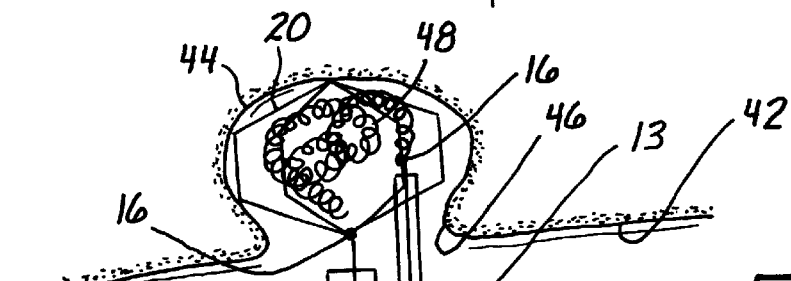
Figure 2D:
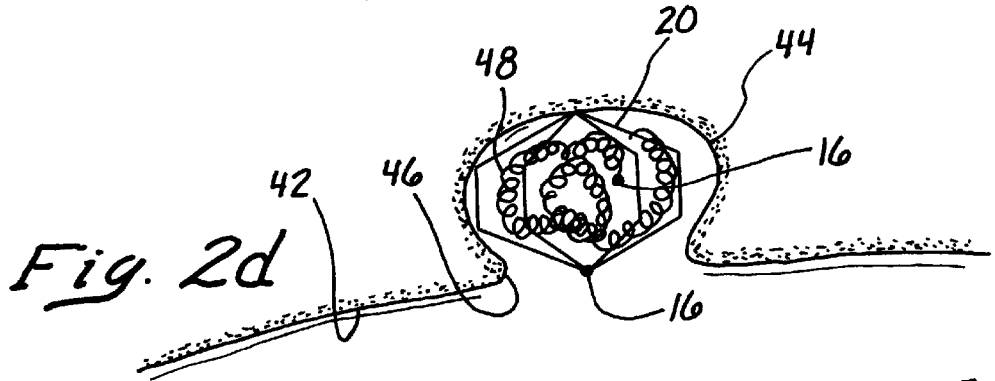

The basic structure of GDC cage assembly 10 now having been described in connection with FIGS. 6a and 6b and its deployment illustrated in connection with FIGS. 1a and 1b, consider other examples of its application as shown in FIGS. 2–5b. FIG. 2 is a simplified cut-away view of GDC cage assembly 10 shown in a vessel branch in which access is made through a first vessel 40 communicating with a second vessel 42 in which an aneurysm 44 has developed. The particular vascular structure illustrated in FIGS. 2a–d is solely by way of illustration and does not in any way limit the type of vascular or cavity sites to which GDC cage assembly 10 may be employed. As shown in FIG. 2a microcatheter 12 is placed with its distal tip at or near opening of neck 46 of aneurysm 44 and GDC cage 20 is deployed beyond the tip of micro-catheter 12 so that cage 20 assumes its expanded configuration as shown in FIG. 1b in aneurysm 44 as illustrated in FIG. 2a. Although cage 20 may have a memorized shape, it is still very soft and compliant as compared to aneurysm 44 and will tend to conform to the shape of aneurysm 44. When formed in the shape of a barrel and when unimpeded by the shape or size of the body lumen into which it is disposed, cage 20 may have an unimpeded maximum diameter of approximately 3 to 30 mm.

The tip of a second microcatheter 13 carrying a GDC coil 48 may then be disposed within aneurysm 44. In the illustrated embodiment the cage catheter 12 is shown as remaining in place with cage 20 still attached. However, it is also possible that cage 20 could be detached and left in aneurysm 44 and microcatheter 12 withdrawn. In both cases, GDC coil 48 will then be deployed into aneurysm 44 using conventional GDC coil catheter 13 as shown in FIG. 2c. As coil 48 is disposed from the end of catheter 13, it expands or coils on itself tending to form a predetermined shape, such as one or more overlapping circular loops. Coil 48 may be from 10 to 300 mm long and have a prebiased memory tending to coil itself in one or more circular loops of 1.5 to 30 mm in diameter. Coil 48 is also very soft and compliant and will tend to conform to the shape of cage 20 and to aneurysm 44. As GDC coil 48 self coils it becomes enmeshed or entangled with cage 20. The expansive force of cage 20 and coil 48 are not sufficient to perforate aneurysm 44 or to otherwise necessarily materially change the shape of aneurysm 44 or to apply undue pressure on the walls of aneurysm 44. The expansive force of coils 48 is also quite low and the shape of cage 20 is not materially altered by it if at all. Coil 48 is then detached from catheter 13 after being properly place and enmeshed in cage 20. If not properly place or enmeshed with cage 20, coil 48 can be withdrawn from aneurysm 44 into catheter 13 and redisposed in aneurysm 44. If not previously detached, cage 20 at this point is then detached and left in place with retained coil 48 as shown in FIG. 2d.

Although the illustrated embodiment has described the placement and retention of a single coil 48, it is expressly contemplated that a multiple number of coils 48 will be disposed into cage 20. Cage 20 is preferably detached from catheter 12 after the implantation of the last of the multiple number of coils 48.

Because of the configuration and size of cage 20, the length of coils 48 and their self-coiling or twisting bias or memory, the escape of coils 48 from aneurysm 44 is impossible or at least improbable, notwithstanding the velocity of blood flow which may be passing by neck 46 or the blood turbulence which may be introduced into aneurysm 44 from either vessels 42 or 40 through neck 46. In some cases this flow or turbulence is sufficient to eventually wash one or more coils 48 from aneurysm 44 unless cage 20 is deployed into aneurysm 44.

Thus in the preferred embodiment cage structure 20 is deployed first into aneurysm 44 and a plurality of GDC coils 48 deployed thereafter, since when in the expanded configuration spacing between the wires of cage structure 20 is still sufficient to allow the insertion of one or more GDC coils 48. However, once the GDC coil 48 has been deployed into cage 20, the length and flexibility of GDC coil 48 causes it to become positioned into an interfering orientation with the wires of cage 20. In this way, coils 48 are snared or entrapped within aneurysm 44 notwithstanding the fact that there still may be blood flow or turbulence within aneurysm 44 which might otherwise tend to wash coils 48 from it.

Figure 3:
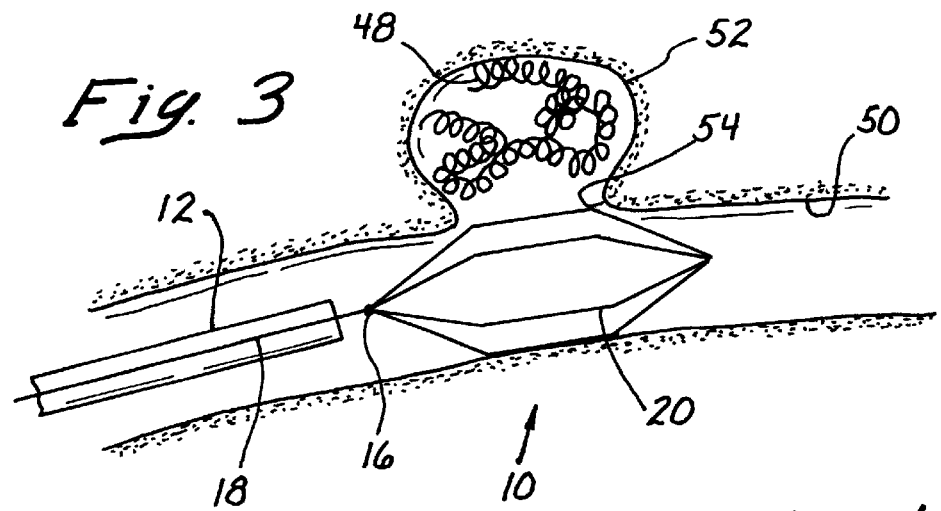
FIG. 3 is a diagrammatic cut-away side elevational view of the first embodiment of the GDC cage used as a retaining barrier in the parent vessel in order to prevent the escape of the GDC coils which have been disposed into an adjacent connected aneurysm.

A second application of GDC cage assembly 10 is depicted in the side cut-away view of FIG. 3, showing a vessel 50 and aneurysm 52. In this situation cage 20 has been deployed across an opening or neck 54 of aneurysm 52 during the delivery of GDC coils 48 within aneurysm 52. Cage 20 is then detached and left at the place serving as a fence, grating or barrier through which coils 48 cannot pass. The open structure of cage 20 is such that it does not substantially impede blood flow within vessel 20, but the spacing between the wires of cage 20 are sufficiently close to ensnare any coil 48 which has moved to an interfering position which will snag on the wires of cage 20. Alternately, the cage may not be detached at all, but may be withdrawn at the end of the implantation of the coils, which have occluded the aneurysm or at least so enmeshed or tangled with each other as to be securely retained within the aneurysm.

A third application of GDC cage assembly 10 is depicted in the diagrammatic side cut-away view of FIG. 4, wherein GDC coil assembly 10 is shown in vessel 56 in which an aneurysm 58 has formed. In this instance, a GDC coil 48 has escaped from aneurysm 58 and has moved downstream in the direction of blood flow 60. Microcatheter 12 is inserted into the illustration of FIG. 4 and moved past the opening of aneurysm 58 to the location of escaped GDC coil 48 where cage structure 20 is then deployed, if not earlier. Coil 48 typically is at least temporarily stopped downstream in the vascular system by a narrowing of the vessel or some other geometric feature of the vascular system. Cage 20 entangles with escaped coil 48 when deployed or extended from the tip of catheter 12. If successfully snared, it will then usually be impossible to withdraw cage 20 and GDC coil 48 back within microcatheter 12, but the escaped coil is then firmly ensnared within cage 20 and the entire cage assembly 10 with ensnared coil 48 may then be removed by pulling microcatheter 12.

Figure 8:
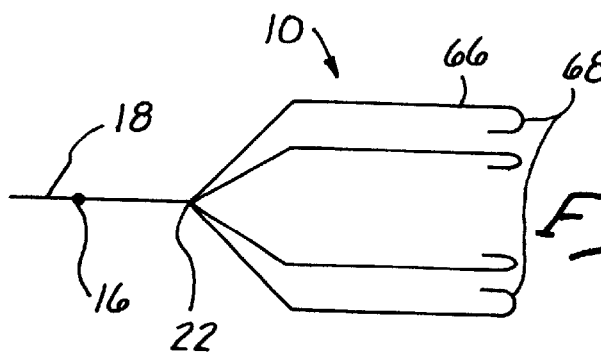
FIG. 8 is a diagrammatic side-elevational view of a third embodiment of the GDC cage shown in an expanded configuration.
Figure 7:
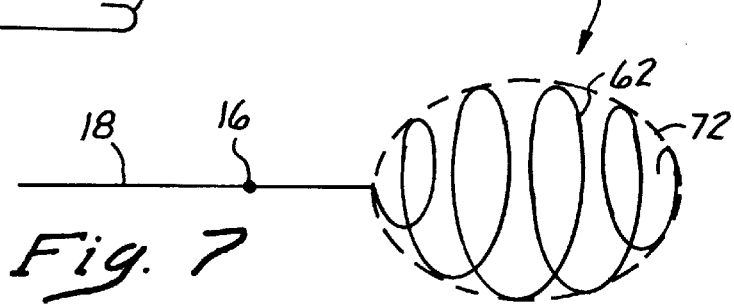
FIG. 7 is a diagrammatic side-elevational view of a second embodiment of the GDC cage shown in its expanded configuration.
Figure 9:
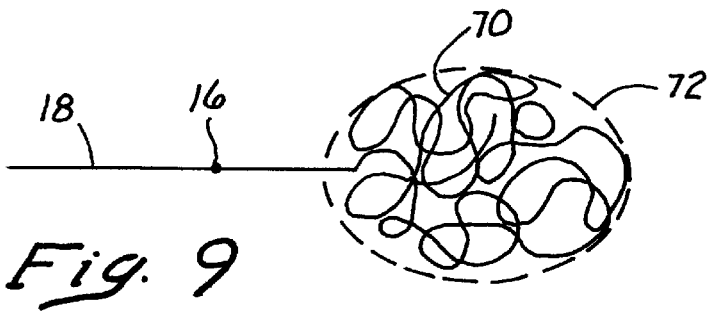
FIG. 9 is a diagrammatic side-elevational view of a fourth embodiment of the GDC cage shown in an expanded configuration.

Turn now to consider an alternative embodiment for cage structure 20 as shown in FIGS. 7–9. In FIG. 7 the bird cage of barrel-shaped cage 20 of FIGS. 1a–5b is replaced by a helical wire 62 whose envelope conforms to a predetermined three dimensional shape. For example, in the embodiment of FIG. 7, helical wire 62 whose envelope conforms to a predetermined three-dimensional shape. For example, in the embodiment of FIG. 7, helical wire 62 is formed so that when it is deployed and expands, it expands to a generally spherical envelope. Many different envelope shapes can be deployed, if desired, including conical, biconical, cylindrical, elliptical, spherical and arbitrarily free-formed solids of revolution or entirely random three-dimensional shapes. The envelope can be defined by conventional means by forming and heat treating wire 62 on a mandrel, having the desire envelope shape. FIG. 7 represents a form of GDC cage 20 which may be useful in the applications of FIGS. 2a–d and 3.

GDC cage assembly 10 is shown in FIG. 8 in which wire cage 20 is replaced by a hooked wire cage 64 shown here in the form of a fruit-picking basket. The proximal ends of wires 66 may be joined as before in an proximate joint 22 from which they then diverge to form a plurality of diverging fingers ending in one or more hooks 68. The hooks may be inwardly turned in order to avoid catching on the interior walls of the vessel or may be outwardly deployed to increase its ability to snag escaped coils or both. Again, cage 64 is relatively soft and deformable and therefore no tissue damage or perforation is possible or likely because of hooks 68. In general cage 20, 62 or 64 will be softer than the tissue next to which it is deployed. The embodiment of FIG. 8 is a form of GDC cage assembly 10 which would have particular utility in the application of FIG. 4.

FIG. 9 is a side perspective view of a fourth embodiment of GDC cage assembly 10 in which wire cage 20 has been replaced by a random bird's nest or ball of string configuration 70. Random cage 70 may be completely arbitrarily formed or conformed to a predetermined envelope 72 as described in connection with FIG. 7. The embodiment of GDC cage assembly 10 in FIG. 9 is of particular utility in the application of FIGS. 2a–d Although GDC cage assembly 10 has been described as having utility in connection with use with GDC coils 48, the embodiment of at least FIGS. 6a and 6b also has utility as a radio frequency probe for shrinking vessels or large lumens. As shown in FIG. 5a, GDC cage assembly 10 is disposed within a large lumen or vessel 74. Electrical current or RF energy is applied from RF source 76 to cage 20 which serves as an radiating antenna. Electromagnetic energy is absorbed in the proximate tissue to create dielectric heating which causes vessel 74 to collapse as shown in FIG. 5b. Because of the collapsible nature of cage 20, cage 20 freely collapses in response to the shrinkage of the adjacent vessel 74 without causing any tissue damage. In this way diathermic shrinking is achieved without exposing the shrinking tissue to mechanical interference, injury or abrasion from the RF probe. The cage is then detached and left in the occluded lumen.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An apparatus for use within a body lumen comprising:
   a wire;
   a selectively detachable joint;
   an expandable cage, said joint coupling said cage to said wire; said expandable cage capable of assuming a collapsed and expanded configuration, said expanded configuration being self-assumed by said cage when said cage is freed of confinement,
   whereby, said cage expands for deployment within said body lumen.

2. The apparatus of claim 1 further comprising a catheter, said wire and expandable cage being selectively disposable within said catheter when said cage assumes said collapsed configuration and selectively disposable outside of said catheter wherein said cage assumes said expanded configuration.

3. The apparatus of claim 2 wherein at least one coil is disposable in said body lumen and wherein said cage is adapted to return said coil within said body lumen when said cage is in said expanded configuration.

4. The apparatus of claim 3 wherein said body lumen is an aneurysm and said catheter being used to position said cage into said aneurysm, said cage assuming said expanded configuration as such cage is being disposed from said catheter into said aneurysm, said coil being disposable in said aneurysm and retained therein by said cage.

5. The apparatus of claim 3 wherein said cage is disposable from said catheter across said opening of said aneurysm in a parent vessel communicated to said aneurysm, said aneurysm having an opening, said cage acting as a retaining grate across said opening to prevent escape of said free coil from said aneurysm.

6. The apparatus of claim 2 wherein said body lumen is a vessel and said free coil is disposable in said vessel, said cage being adapted to capture said free coil in said vessel when said cage is in said expanded configuration to allow said captured free coil to be removed with said cage from said vessel.

7. The apparatus of claim 1 further comprising a source of radio frequency energy coupled to said wire so that said radio frequency energy is coupled to and emitted from said cage into said body lumen to diathermally heat and thereby shrink said body lumen while said cage tends to assume said collapsed configuration according to shrinkage of said body lumen.

8. The apparatus of claim 1 wherein said cage is comprised of a plurality of wires having a memory so that when said cage is free of confinement, it assumes a prebiased shape memorized by said plurality of wires.

9. The apparatus of claim 8 wherein said cage is comprised of a plurality of wires in the form of a cylindrical barrel.

10. The apparatus of claim 9 wherein said cylindrical barrel cage has bottom and top apexes where said plurality of wires are commonly joined together.

11. The apparatus of claim 1 wherein said detachable joint is electrolytically disintegrated to detach said wire from said cage.

12. The apparatus of claim 1 wherein said detachable joint is an electrolytically disintegratable region.

13. The apparatus of claim 11 wherein said detachable joint is an electrolytically disintegratable bead.

14. The apparatus of claim 12 wherein said electrolytically disintegratable region comprises a flexible electrolytically disintegratable coil coupled between said wire and said cage.

15. The apparatus of claim 14 wherein said electrolytically disintegratable region further comprises a tapered tip of said wire extending through said coil and coupled to said cage.

16. The apparatus of claim 1 wherein said cage comprises a plurality of wires, each wire having two ends, one end of each said wires being coupled together in a common apex and opposing ends of which are free, each said opposing free end forming a curved hook shape.

17. The apparatus of claim 1 wherein said cage comprises a helical coil which when in said expanded configuration is contained within an envelope of predetermined three-dimensional shape.

18. The apparatus of claim 1 wherein said cage comprises at least one randomly-shaped wire, which when in said expanded configuration is contained within an envelope of predetermined three-dimensional shape.

19. An RF probe for shrinking a body lumen comprising:
a wire;
an collapsible cage coupled to said wire, said cage capable of assuming an expanded configuration and a collapsed configuration, including a continuous deformation of configurations therebetween, said cage adapted to radiate radio frequency energy to tissue surrounding said body lumen to diathermally heat and shrink said tissue and lumen, said cage having a substantial resiliency so that when free of confinement said cage normally assumes said expanded configuration, and when confined by shrinking of said tissue and lumen, said cage assumes said collapsed configuration and is conformable to said tissue during shrinkage of said lumen.

* * * * *